(12) United States Patent
Kimura et al.

(10) Patent No.: US 6,584,854 B2
(45) Date of Patent: Jul. 1, 2003

(54) PRESSURE SENSOR AND PRESSURE-MEASURING APPARATUS USING PRESSURE BUFFERING

(75) Inventors: Isamu Kimura, Kyoto (JP); Masatoshi Oba, Kyoto (JP); Takashi Itakura, Kyoto (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 10/175,520

(22) Filed: Jun. 19, 2002

(65) Prior Publication Data
US 2003/0056598 A1 Mar. 27, 2003

(30) Foreign Application Priority Data
Jun. 19, 2001 (JP) ........................ 2001-185675

(51) Int. Cl.[7] .............................. G01L 9/00; G01L 9/16
(52) U.S. Cl. ........................................................ 73/754
(58) Field of Search ........................... 73/754, 715–756; 338/2, 4, 42; 361/283.1–283.4

(56) References Cited
U.S. PATENT DOCUMENTS
5,062,302 A * 11/1991 Petersen et al. ............... 73/754

OTHER PUBLICATIONS
"Hoechst Celanese, Foamex Announce New Superabsorbant Foam Technology", Nonwovens Mark., 1989, vol. 4, No. 14, p. 3. (No month).

* cited by examiner

Primary Examiner—William Oen
(74) Attorney, Agent, or Firm—Rosenthal & Osha L.L.P.

(57) ABSTRACT

A pressure-detecting chamber 23, a pressure-directing path 25 and a buffer space 24 are formed on the upper face of a main-body-side substrate 22 as recessed portions, and the upper face of the pressure-detecting chamber 23 is covered with a thin-type diaphragm 31, and upper faces of the pressure-directing path 25 and the buffer space 24 are covered with a cover substrate 30. A pressure-introducing unit 26 formed on the lower face of the main-body-side substrate 22 is connected to the lower face of the buffer space 24. The cross-section of the buffer space 24 is greater than the cross-section of the pressure-introducing unit 26, and the capacity of the buffer space 24 is greater than the capacity of the pressure-directing path 25. With this arrangement, it is possible to provide a pressure sensor which can control the response characteristic of the pressure sensor to a pressure change with high precision without causing serious adverse effects on the other characteristics of the pressure sensor, without preventing the miniaturization of the sensor.

11 Claims, 11 Drawing Sheets

PRESSURE SENSOR AND PRESSURE-MEASURING APPARATUS USING PRESSURE BUFFERING

BACKGROUND OF INVENTION

The present invention relates to a pressure sensor and a pressure-measuring apparatus. In particular, the present invention concerns a pressure sensor which detects a pressure by detecting a distortion of a thin-film diaphragm due to an introduced pressure, and a manufacturing method of such a pressure sensor. Moreover, it also concerns a pressure-measuring apparatus using such a pressure sensor.

Figure 1:
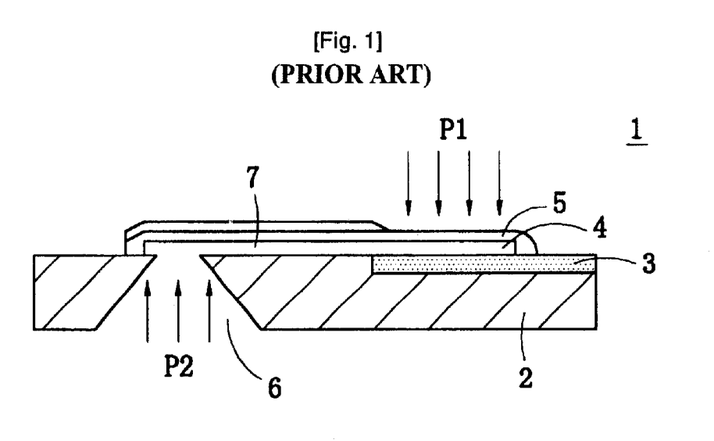
FIG. 1 is a cross-sectional view that shows a structure of a conventional semiconductor pressure sensor of a relative-pressure type.

FIG. 1 is a cross-sectional view that shows a structure of a conventional semiconductor pressure sensor of a relative-pressure type (Japanese Patent Application National Publication No. 8-501156). In this semiconductor pressure sensor 1, a doping area 3 that has a conductive type reversed to the substrate 2 is formed on a semiconductor substrate 2, and a diaphragm 5 is formed with a pressure-detecting chamber 4 located in between. Moreover, a pressure-introducing unit 6, which is formed in the semiconductor substrate 2 through antistropic etching, is connected to a pressure-detecting chamber 4 through a pressure-directing path 7.

When, upon application of a pressure P1 (for example, reference pressure) to the outer surface of the diaphragm 5, the resulting pressure P2, introduced through the pressure-introducing unit 6 and the pressure-directing path 7, is applied to the inner face of the diaphragm 5, the diaphragm 5 is distorted by a pressure difference P2–P1. This distortion allows the distance between the diaphragm 5 and the doping area 3 to change, thereby causing the electrostatic capacity between the diaphragm 5 and the doping area 3 to change; thus, based upon this capacity change, it is possible to detect the pressure difference or the pressure.

In the case when such a pressure sensor 1 is used for detecting a varying pressure, as the frequency of pressure variation in the pressure-detecting chamber 4 becomes higher, the shifting speed of a gas comes to have a determined rate, causing the diaphragm to fail to follow it and to distort. The frequency of the applied pressure at this time is referred to as a cut-off frequency.

Depending on applications, the cut-off frequency or the response frequency of the pressure sensor needs to be designed to have a value suitable for the corresponding purpose, and in the manufacturing process, this needs to be controlled to a target value. For example, in the case of the application to a blood pressure meter, etc., since a pump is used to send air to the cuff belt at a constant rate or to reduce the pressure of the cuff belt at a constant rate, the cut-off frequency of the pressure sensor needs to be set higher than the frequency of pulse waves as well as lower than the frequency of pressure noise so as not to allow the pressure sensor to detect the pressure noise from this pump.

The response characteristic or the cut-off frequency of such a pressure sensor is determined by the capacity of the pressure-detecting chamber and the length or the cross-sectional area of the pressure-directing path 7. However, when an attempt is made to control the response characteristic by using the capacity of the pressure-detecting chamber, characters other than the response frequency of the pressure sensor is to change. For example, when the capacity of the pressure-detecting chamber is changed, problems are raised in which there is a change in the area of the diaphragm and there is a change in the gap thickness between the thin-film diaphragm and the doping area, resulting in deviations in the sensitivity of the pressure sensor. Moreover, in a method in which the length of the pressure-directing path is made longer, since the corresponding area is required on the semiconductor substrate, this prevents miniaturization of the pressure sensor. Furthermore, since, in general, the cross-sectional area of the pressure-directing path is as small as several $\mu m^2$, an attempt to control the response characteristic of the pressure sensor by using the cross-sectional area of the pressure-directing path tends to cause serious deviations in the response characteristic of the sensor unless it is manufactured with very high machining precision.

SUMMARY OF INVENTION

In one aspect, the present invention has been devised to solve the above-mentioned problems, and its objective is to provide a pressure sensor which can control the response characteristic of the pressure sensor in response to a pressure change without causing any adverse effects on the other properties of the pressure sensor and preventing miniaturization of the pressure sensor.

In another aspect, the present invention relates to various pressure-measuring apparatuses including blood-pressure meters, which are not susceptible to pressure noise derived from pumps, etc.

The pressure sensor in accordance with the present invention, which is provided with a thin-film diaphragm and a cavity that is used for detecting pressure, and formed adjacent to said thin-film diaphragm, which are formed in a sensor main body, is designed to detect a pressure introduced to said pressure detecting cavity based upon the amount of distortion of said thin-film diaphragm, and in this arrangement, a pressure-directing path, which connects a pressure-introducing unit formed in said sensor main body to the pressure-detecting-use cavity so as to direct a pressure from the pressure-introducing unit to the pressure-detecting-use cavity, is formed in the sensor main body, and a space having a cross-sectional area greater than the pressure-directing path is formed in the pressure-directing path. Here, the capacity of this space is preferably designed to be greater than the capacity of the pressure-directing path between the space and the pressure-detecting-use cavity.

In the pressure sensor of the present invention, since the space having a cross-sectional area greater than the pressure-directing path is placed in the pressure-directing path connecting the pressure-introducing unit and the pressure-detecting-use cavity, the pressure (flow of gas), transmitted through the pressure-directing path, is delayed in the space; therefore, even in the event of a temporarily or instantaneous pressure change, the pressure change is absorbed in the space, and prevented from reaching the thin-film diaphragm. Therefore, the formation of the above-mentioned space in the pressure-directing path allows the pressure-directing path to have functions of a low-pass filter to pressure. Further, by adjusting the cross-sectional area and the capacity of the space, the degree of delay of the pressure transmission is controlled so that it becomes possible to control the response frequency and cut-off frequency of the pressure sensor with high precision.

In one embodiment, in the pressure sensor of the present invention, the capacity of the space is determined so as to make the sensor response frequency higher than frequencies in a pressure detection range and lower than frequencies in pressure noise; therefore, it is possible to detect the detection pressure or the varied frequency thereof with high precision without having adverse effects from the pressure noise.

In the case of blood-pressure meters, the frequency of pulse waves to be detected is approximately 15 Hz, while the frequency of pressure noise caused by pumps and valves is approximately 50 Hz; therefore, the response frequency of the pressure sensor is set in a range from not less than 25 Hz that is not less than 1.5 times the maximum frequency of the frequency of the detection pressure or the detection pressure range to not more than 35 Hz. Thus, by setting the sensor response frequency to not less than 1.5 times the maximum frequency of the detection pressure area, it becomes possible to provide a pressure sensor that is particularly suited for the application as blood pressure meters.

In another embodiment, in the pressure sensor in accordance with the present invention, the sensor main body is formed by bonding a first substrate and a second substrate to each other, with the pressure-detecting-use cavity and the space being formed on the surface of the first substrate as recessed portions that are covered with the second substrate; therefore, the pressure-detecting-use cavity and the above-mentioned space are formed by simply processing the surface of the first substrate and then joining the second substrate to the first substrate so as to cover it with the second substrate, thereby making it possible to simplify the manufacturing process.

Furthermore, in this embodiment, the space is formed as a recessed portion deeper than the pressure-detecting-use cavity; thus, it becomes possible to make the cross-sectional area of the above-mentioned space greater than the cross-sectional area of the pressure-detecting-use cavity without widening the width of the above-mentioned space, and consequently to miniaturize the pressure sensor since the occupied area of the above-mentioned space is not widened.

In another embodiment, in the pressure sensor in accordance with the present invention, since the above-mentioned pressure-introducing unit is designed so that it has an opening area on the outer side that is wider than an opening area thereof on the inner side, it becomes possible to easily form the pressure-introducing unit by etching (in particular, antistropic etching on the silicon substrate) the semiconductor substrate constituting the sensor main body.

In another embodiment, in the pressure sensor of the present invention, the above-mentioned space may be placed at a position that is in contact with said pressure-introducing unit or in the middle of said pressure-directing path. In either of the cases, since the above-mentioned space is not adjacent to the pressure-detecting-use cavity, it is possible to make the characteristics of the pressure sensor less susceptible to influences from the space. Further, in the case when the above-mentioned space is placed at the position in contact with the pressure-introducing unit, it is only necessary to place the pressure-directing path only on one-side of the above-mentioned space; thus, it becomes possible to miniaturize the pressure sensor. Moreover, when the above-mentioned space is placed in the middle of the pressure-directing path as described in the latter case, even upon invasion of dusts, etc. through the pressure-introducing unit, these are caught in the space and less likely to reach the pressure-detecting-use cavity, thereby making it possible to reduce the adverse effects of dusts, etc. on the sensor characteristics. Here, in the case when the above-mentioned space is placed at a position adjacent to the pressure-introducing unit, an arrangement is made so that the pressure-introducing unit and the above-mentioned space are aligned in the thickness direction of the sensor main body; thus, it is possible to reduce the installation spaces of the two members, and consequently to miniaturize the pressure sensor.

In another embodiment, in the pressure sensor of the present invention, a plurality of pressure-detecting-use cavities connected by a pressure-directing path are placed, and the space is formed in a pressure-directing path that reaches from the pressure-introducing unit to the first pressure-detecting-use cavity; therefore, it becomes possible to reduce the portions in which the above-mentioned spaces are formed, and consequently to miniaturize the pressure sensor.

In another embodiment, in the pressure sensor of the present invention, a plurality of pressure-detecting-use cavities connected by a pressure-directing path are placed, and the above-mentioned space is formed at a position before a portion at which the pressure-directing path extended from said pressure-introducing unit is branched to the respective pressure-detecting-use cavities; therefore, it becomes possible to reduce the portions in which the above-mentioned spaces are formed, and consequently to miniaturize the pressure sensor.

The pressure-measuring apparatus of the present invention is provided with a pressure sensor disclosed in the present invention; and a calculation circuit for calculating a pressure value from electric signals that are outputted in accordance with the pressure detected by the pressure sensor.

In one embodiment of the pressure-measuring apparatus of the present invention, since it is possible to eliminate pressure noise that is caused by a pump and a valve, it becomes possible to positively hold pulse waves that form a pressure to be detected, and consequently to achieve a blood pressure meter that has a high S/N ratio. Moreover, since it is not necessary to provide circuits, etc. that electrically eliminate noises, it is possible to miniaturize the pressure sensor, and consequently to achieve low prices. In particular, in the case of the application to a pressure sensor used for fingers, it is possible to miniaturize the blood pressure meter, and consequently to provide a convenient meter in use.

Additionally, the constituent elements as described above can be desirably combined as widely as possible.

DETAILED DESCRIPTION

First Embodiment

Figure 2A:
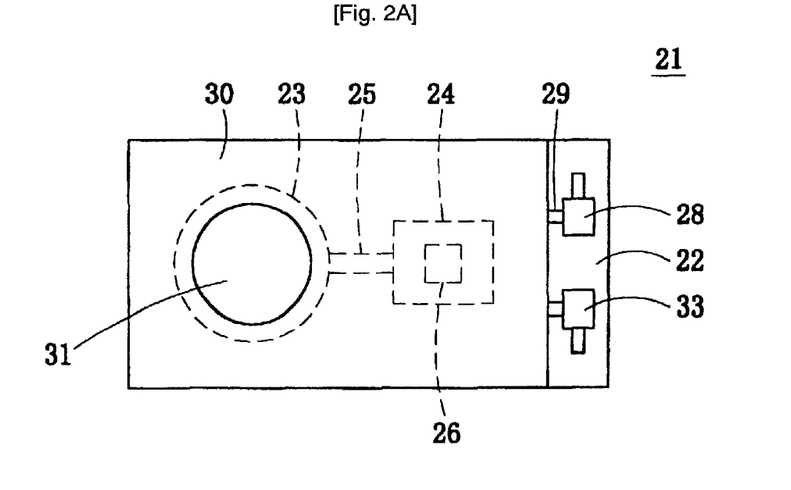
FIG. 2A is a plan view and a cross-sectional view that show a structure of a pressure sensor of the present invention.
Figure 2B:
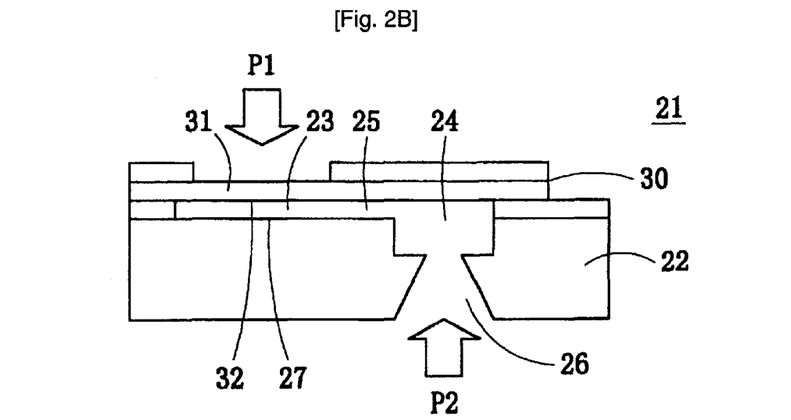
FIG. 2B is a plan view and a cross-sectional view that show a structure of a pressure sensor of the present invention.
Figure 3:
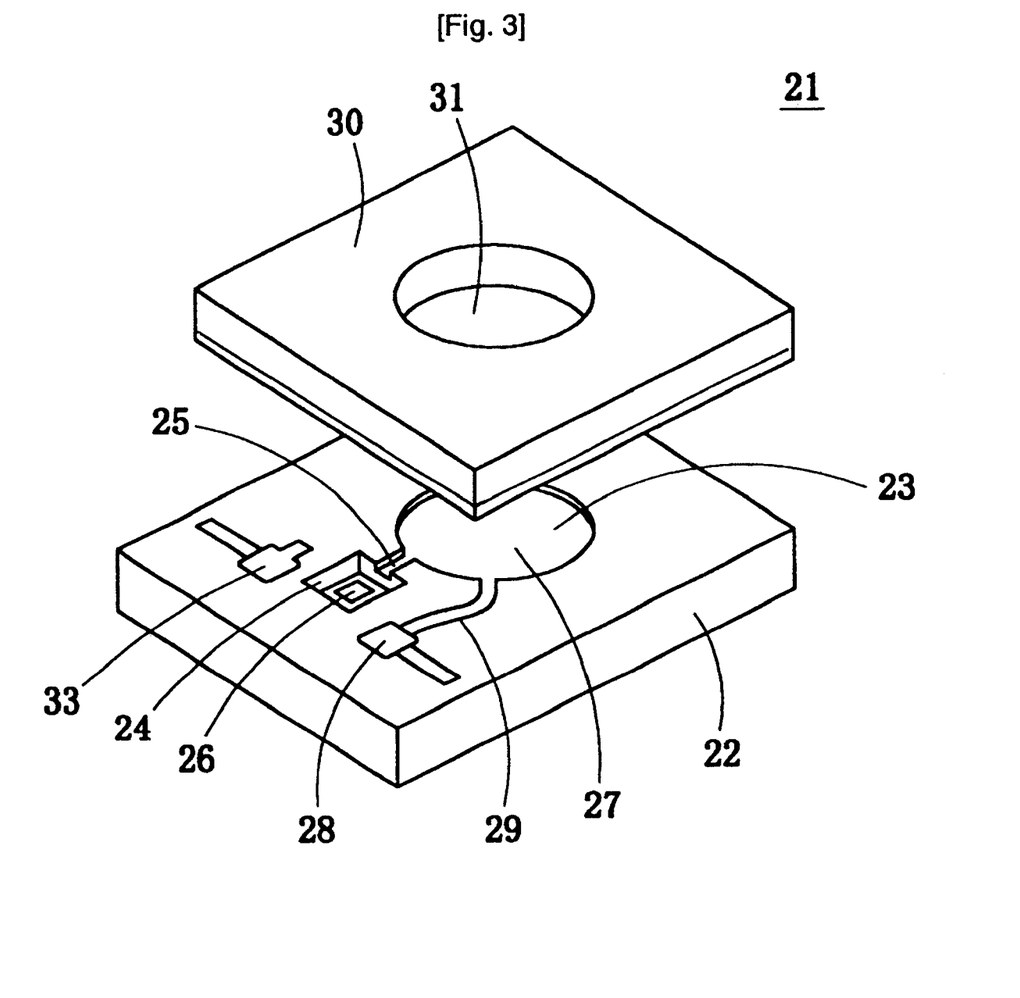
FIG. 3 is an exploded perspective view of the pressure sensor of the present invention.

FIGS. 2A and 2B are a plan view and a cross-sectional view showing a structure of a pressure sensor 21 that is one embodiment of the present invention, and FIG. 3 is an exploded perspective view thereof. In this pressure sensor 21, a round pressure-detecting chamber 23 and a square buffer space (or buffer concavity) 24 are formed on the upper face of a main-body side substrate 22 as recessed portions, and the pressure-detecting chamber 23 and the buffer space 24 are connected to each other through a straight pressure-directing path 25. Here, the pressure-detecting chamber 23 and the pressure-directing path 25 have the same depth, while the buffer space 24 is deeper than the pressure-detecting chamber 23 and the pressure-directing path 25. The cross-sectional area of the buffer space 24 is greater than the cross-sectional area of the pressure-directing path 25, and the capacity of the buffer space 24 is greater than the capacity of the pressure-directing path 25. Since the buffer space 24 is deeper than the pressure-directing path 25, it is possible to make the cross-sectional area and the capacity greater without the necessary of widening the width thereof so much in comparison with the width of the pressure-directing path 25, and consequently to miniaturize the pressure sensor 21.

Moreover, a pressure-introducing unit (or passage) 26 having a truncated pyramid shape is provided on the under surface of the main-body-side substrate 22 through etching, and the lower face of the pressure-introducing unit 26 is opened to the lower face of the main-body-side substrate 22, with the upper face of the pressure-introducing unit 26 being opened to the inside of the buffer space 24. Therefore, the buffer space 24 is formed adjacent to the pressure-introducing unit 26 so that the pressure-introducing unit 26 is connected to the pressure-detecting chamber 23 through the buffer space 24 and the pressure-directing path 25. Here, the pressure-introducing unit 26 has a greater opening area on the lower face and a smaller opening area on the upper face of the inside contacting the buffer space 24.

A fixed electrode 27 is formed on the bottom face of the pressure-detecting chamber 23, and an electrode pad 28 attached to the upper face of the main-body-side substrate 22 and the fixed electrode 27 are connected to each other by an electrode pattern 29.

A cover substrate 30 is superposed on and joined to the upper face of the main-body-side substrate 22. The pressure-detecting chamber 23, the buffer space 24 and the pressure-directing path 25 of the main-body-side substrate 22 are sealed by the cover substrate 30, and a round thin-type diaphragm 31 is formed at a position of the cover substrate 30 facing the pressure-detecting chamber 23. A movable electrode 32 is formed on the inner face of the thin-type diaphragm 31 by a metal thin film, etc., and the movable electrode 32 is allowed to conduct to an electrode pad 33 formed on the upper face of the main-body-side substrate 22.

Thus, in this pressure sensor 21, when, upon application of a pressure P1 (for example, reference pressure) on the upper face of the thin-type diaphragm 31, the resulting pressure P2 is introduced into the pressure-detecting chamber 23 from the pressure-introducing unit 26, the thin-type diaphragm 31 is distorted by the pressure difference P1–P2 with the result that the electrostatic capacity between the fixed electrode 27 and the movable electrode 32 is changed; thus, by detecting the change in the electrostatic capacity, the pressure difference P1–P2 or pressure P2 measured based upon P1 as reference pressure is detected.

Moreover, by forming the buffer space 24 between the pressure-directing path 25 and the pressure-introducing unit 26, the pressure, applied to the pressure-directing path 25, is delayed and deviations, etc. of the machining precision of the pressure-introducing unit 26 are absorbed, and even in the event of a temporarily or instantaneous pressure change, this change is absorbed by the buffer space 24 so as to suppress the reaction of the thin-type diaphragm 31. Even in the event of a continuous pressure change with a high frequency, the pressure-directing path 25 serves as resistance in accordance with the size thereof, and regulates the transmission of the pressure, thereby suppressing the reaction of the thin-type diaphragm 31. Therefore, the reaction of the thin-type diaphragm 31 is regulated by two stages of the buffer space 24 and the pressure-directing path 25 so that it becomes possible to obtain a desired pressure response characteristic depending on the sizes of the buffer space 24 and the pressure-directing path 25. Moreover, in the case when the frequency of the detection pressure is lower than the frequency of pressure noise, it is possible to eliminate the pressure noise.

In the case of blood-pressure meters in which pulse waves are detected, since the pressure noise generated in a pump, a valve, etc. is absorbed in buffer space 24 and is not transmitted to the pressure-detecting chamber 23, it is possible to detect the pulse waves with high precision without intervention by pressure noise. The frequency of pulse waves is approximately 15 Hz, while the frequency of pressure noise caused by pumps and valves is approximately 50 Hz; therefore, the response frequency of the pressure sensor is set in a range from not less than 25 Hz that is not less than 1.5 times the maximum frequency of the frequency of the detection pressure or the detection pressure range to not more than 35 Hz. This response frequency (cut-off frequency) can be adjusted by the cross-sectional area and the capacity of the buffer space 24.

Moreover, the adjustment of the response frequency of the pressure sensor using the buffer space 24 is less susceptible to adverse effects on the sensor characteristics in comparison with the adjustment thereof using the pressure-detecting chamber 23, thereby making it possible to provide a superior adjusting method. Furthermore, in comparison with the adjustment thereof using the length, etc. of the pressure-directing path 25, it is not necessary to provide a bigger pressure sensor. Since this arrangement is formed with higher precision in comparison with the pressure-directing path 25, it is possible to reduce deviations in the response frequency.

FIG. 4 is a drawing that explains the manufacturing processes of the above-mentioned pressure sensor 21. Referring to FIG. 4, the following description will discuss the manufacturing processes of the pressure sensor 21. First, an embedded oxide film 35 having a predetermined depth is formed in an area of the silicon substrate 34 (or a glass substrate may be used) at which the buffer space 24 is to be formed (FIG. 4A). Next, the upper face of the silicon substrate 34 is covered with an insulating film 36 in order to insulate the silicon substrate 34 from the cover substrate 30, and the insulating film 36 is removed from areas corresponding to the pressure-detecting chamber 23, the pressure-directing path 25 and buffer space 24. The insulating film 36 is formed by a silicon nitride film 36, etc., by using, for example, an LPCVD method. Consequently, the upper face of the silicon substrate 34 is covered with the insulating film 36 except the areas corresponding to the pressure-detecting chamber 23, the pressure-directing path 25 and the buffer space 24 (FIG. 4B). The main-body-side substrate 22 is constituted by these insulating film 36 and silicon substrate 34.

Figure 4A:
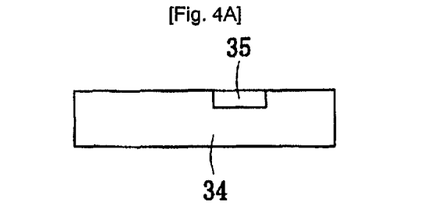
FIG. 4 is a drawing that explains manufacturing processes of the pressure sensor shown in FIG. 2.
Figure 4B:
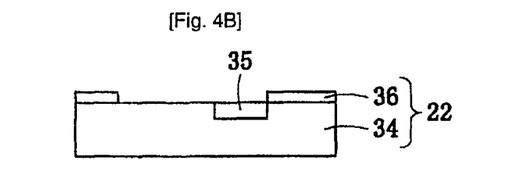
Figure 4C:
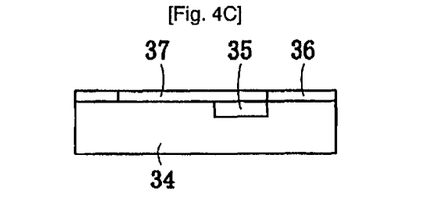

Next, a sacrifice layer 37, made of LTO, etc., is formed on the upper face of the silicon substrate 34 over the insulating film 36, and by patterning the sacrifice layer 37, the sacrifice layer 37 is embedded inside the opening of the insulating film 36 (FIG. 4C). In other words, the layer 37 is embedded to an area that is to form the pressure-detecting chamber 23 and the pressure-directing path 25, with the upper face of the embedded oxide film 35 being covered with the sacrifice layer 37.

Figure 4D:
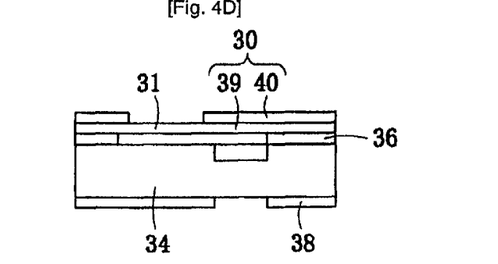

Thereafter, a mask 38, made of an oxide film and a silicon nitride film (SiN), etc., is formed on the lower face of the silicon substrate 34, and the mask 38 is patterned so that the mask 38 is opened at a position in which the pressure-introducing unit 26 is formed. Moreover, a polysilicon film 39 is formed on the upper face of the insulating film 36 and the sacrifice layer 37, a protection film 40, made of LTO, SiN, etc., is formed on the upper face of the polysilicon film 39, and the protection film 40 is patterned so that the polysilicon film 39 is exposed to an area facing the area to form the pressure-detecting chamber 23 (FIG. 4D). Thus, the cover substrate 30 is constituted by the protective film 40 and the polysilicon film 39, and the thin-type diaphragm 31 is formed by a polysilicon film 39 located on an area exposed from the protective film 40.

Figure 4E:
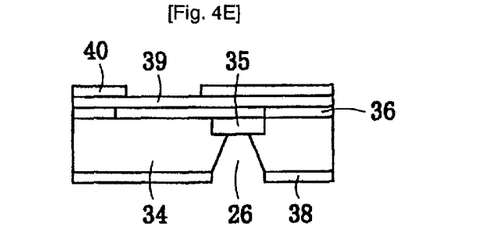
Figure 4F:
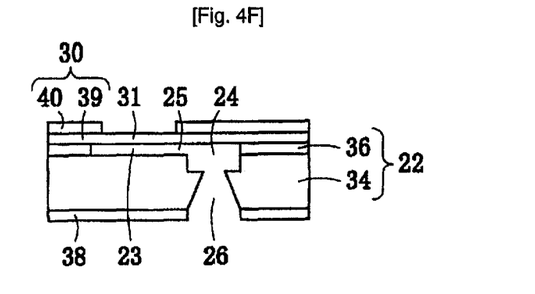
Figure 5A:
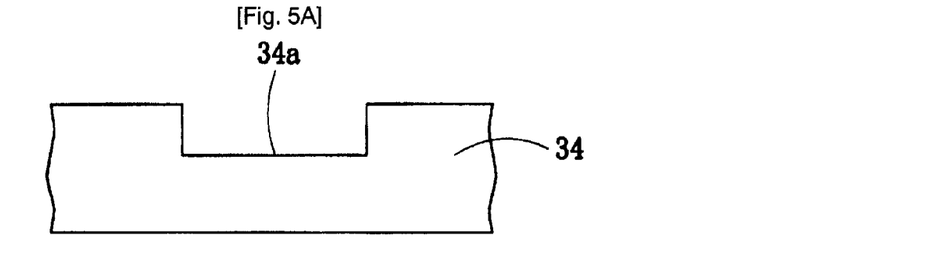
FIG. 5 is a drawing that explains processes in which an embedded oxide film is formed on the surface of a silicon substrate.
Figure 5B:
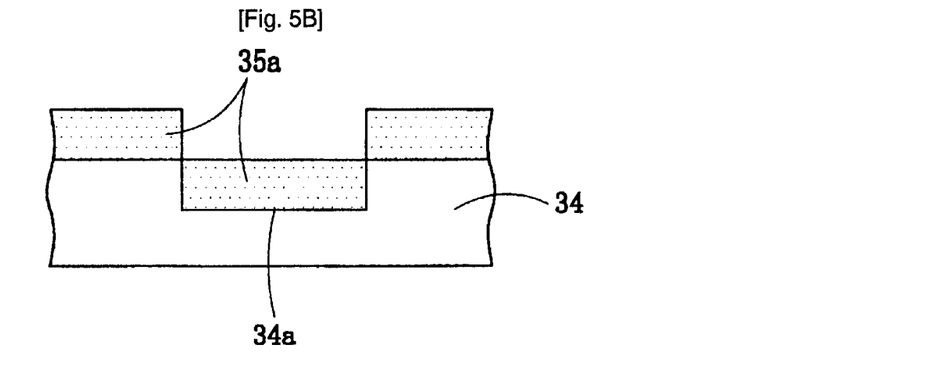
Figure 5C:
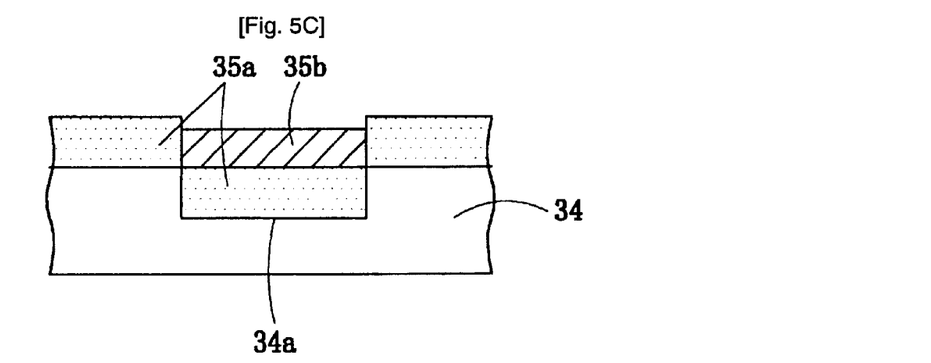
Figure 5D:
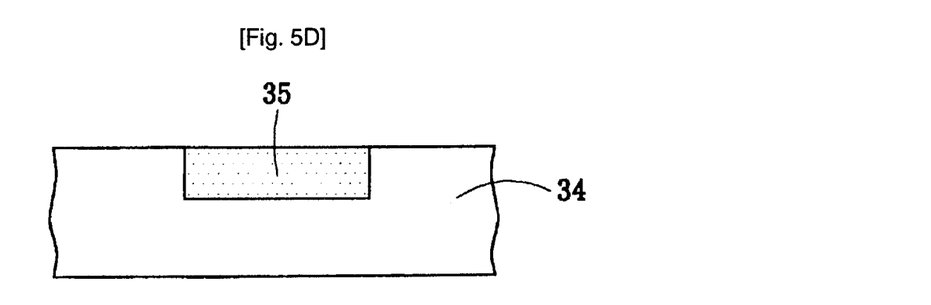

Next, the lower face of the silicon substrate 34 is etched by using etchant such as TMAH, KOH, etc., through the opening of the mask 38 to form the pressure-introducing unit 26 on the lower face of the silicon substrate 34 (FIG. 4E). Further, the embedded oxide film 35 and the sacrifice layer 37 are etched and removed through the pressure-introducing unit 26 so that the pressure-directing path 25 and the pressure-detecting chamber 23 are formed between the main-body-side substrate 22 and the cover substrate 30 (FIG. 4F).

FIG. 5 shows a process (process shown in FIG. 4A) in which the embedded oxide film 35 is formed in the surface of the silicon substrate 34. In other words, a mask (not shown in figures) is formed on the surface of the silicon substrate 34, and a wet etching process using TMAH, etc., or a dry etching process using SF6, etc., is carried out through the opening of the mask so that a recessed portion 34a (with a depth of, for example, 2 $\mu$m)(FIG. 5B) is formed on the surface of the silicon substrate 34. Next, an oxide film 35a is deposited on the silicon substrate 34 with a thickness having the same size as the depth of the recessed portion 34a (FIG. 5B), and resist 35b is further applied onto the oxide film 35a, and the resist 35b is removed from the other areas with only the resist 35b on the oxide film 35a embedded inside the recessed portion 34a being left (FIG. 5C). Thereafter, when buffer hydrofluoric acid is used to etch the oxide film 35a, only the oxide film 35a inside the recessed portion 34a covered with the resist 35b is allowed to remain without being etched; thus, by separating the resist 35b upon completion of the etching, a predetermined embedded oxide film 35 is formed on the surface of the silicon substrate 34 by the oxide film 35a (FIG. 5D).

Figure 6:
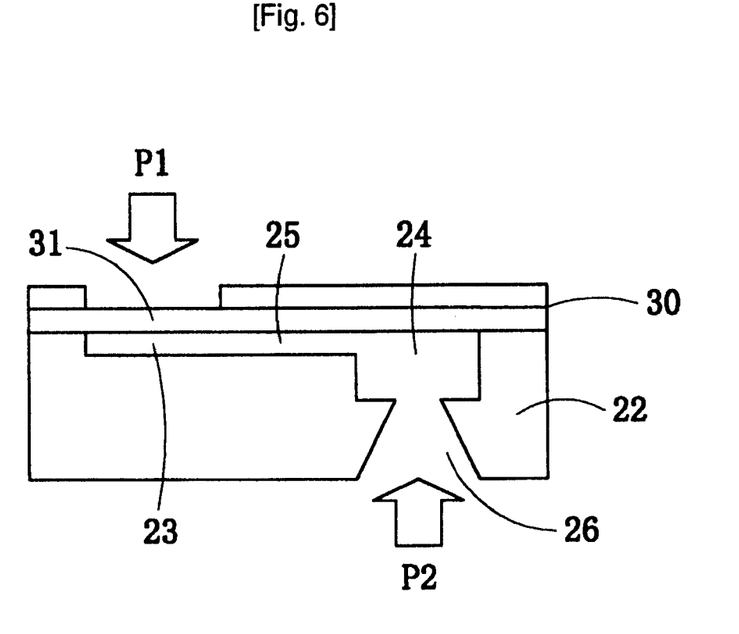
FIG. 6 is a schematic cross-sectional view that shows a structure of a pressure sensor in accordance with another embodiment of the present invention.

Here, in the above-mentioned embodiment, the main-body-side substrate 22 is formed by using a composite material of the silicon substrate. 34 and the insulating film 36; however, as shown in FIG. 6, the main-body-side substrate 22 may be formed by using only the single material of the silicon substrate or the glass substrate, and the silicon substrate or the glass substrate may be etched to form the pressure-detecting chamber 23 and the pressure-directing path 25.

Second Embodiment

Figure 7:
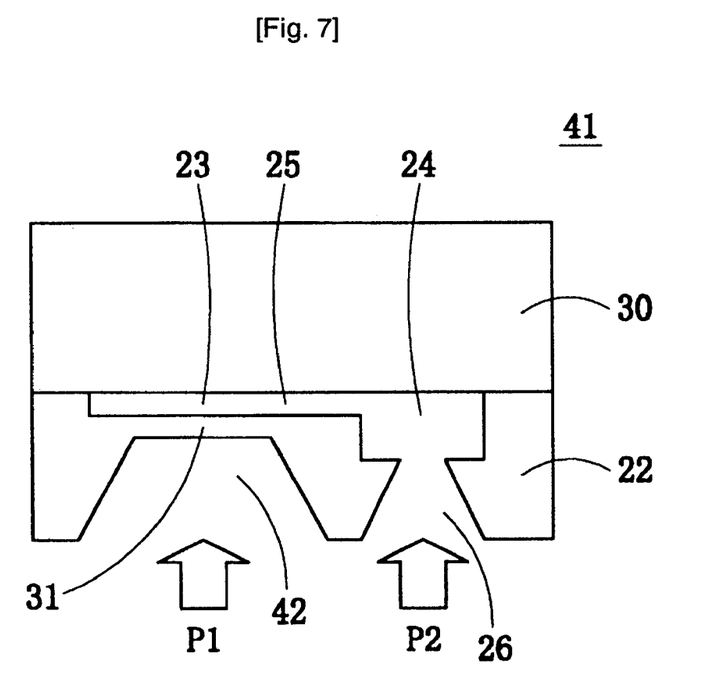
FIG. 7 is a schematic cross-sectional view that shows a structure of a pressure sensor in accordance with still another embodiment of the present invention.

FIG. 7 is a cross-sectional view that shows a construction of a pressure sensor 41 in accordance with another embodiment of the present invention. In this pressure sensor 41, a pressure-detecting chamber 23 is formed on the upper face of a main-body-side substrate 22 made of a silicon substrate, and a pressure-introducing-use recessed portion 42 is formed below the pressure-detecting chamber 23 through a thin-type diaphragm 31 made of a silicon substrate. Moreover, a cover substrate 30 made of a glass substrate is joined to the upper face of the main-body-side substrate 22 so as to seal the pressure-detecting chamber 23, the pressure-directing path 25 and the buffer space 24. With this arrangement, two pressures P1, P2 may be introduced from the same face.

Third Embodiment

Figure 8:
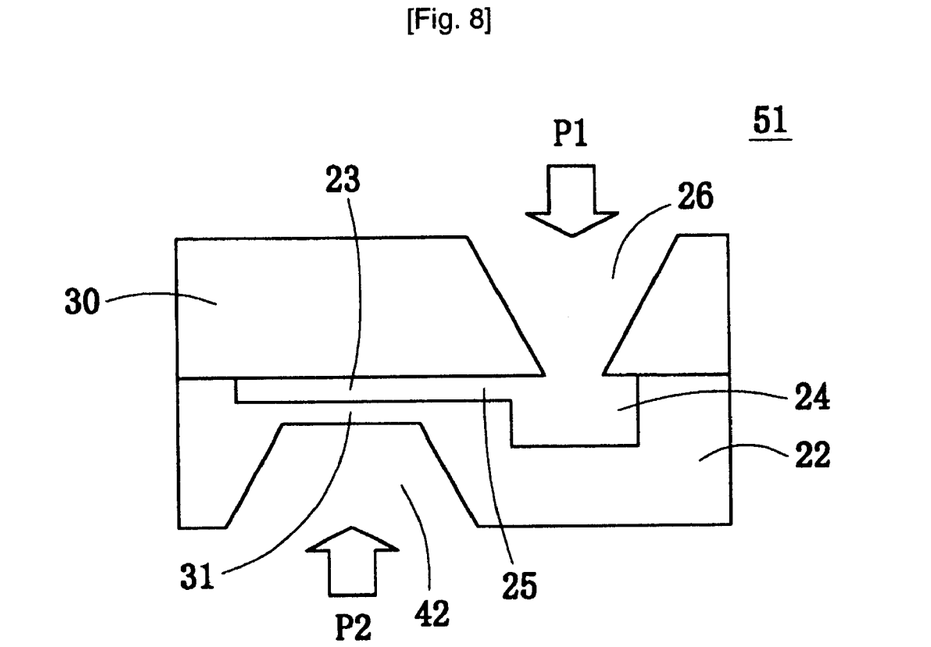
FIG. 8 is a schematic cross-sectional view that shows a structure of a pressure sensor in accordance with still another embodiment of the present invention.

FIG. 8 is a cross-sectional view that shows a structure of a pressure sensor 51 in accordance with still another embodiment of the present invention. In this pressure sensor 51, a pressure-detecting chamber 23 is formed on the upper face of a main-body-side substrate 22 made of a silicon substrate, and a pressure-introducing-use recessed portion 42 is formed below the pressure-detecting chamber 23 through a thin-type diaphragm 31 made of a silicon substrate. Moreover, a cover substrate 30 made of a glass substrate is joined to the upper face of the main-body-side substrate 22 so as to seal the pressure-detecting chamber 23 and the pressure-directing path 25 so that the pressure-directing unit 26 having a tapered shape is placed on the cover substrate 30 so as to be adjacent to the buffer space 24.

Figure 9:
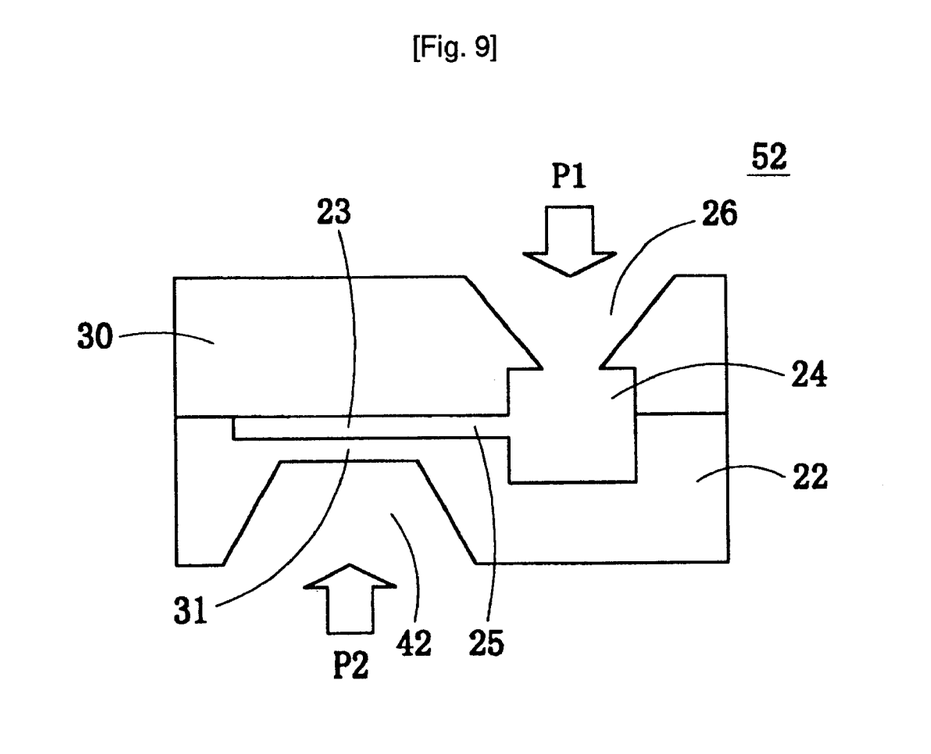
FIG. 9 is a schematic cross-sectional view that shows a structure of a pressure sensor in accordance with still another embodiment of the present invention.

Moreover, in the pressure sensor 52, shown in FIG. 9, which has almost the same structure as the pressure sensor 51 of FIG. 8, the buffer space 24 is placed on the upper face of the main-body-side substrate 22 as well as on the lower face of the cover substrate 30 so as to widen the capacity of the buffer space 24.

Fourth Embodiment

Figure 10:
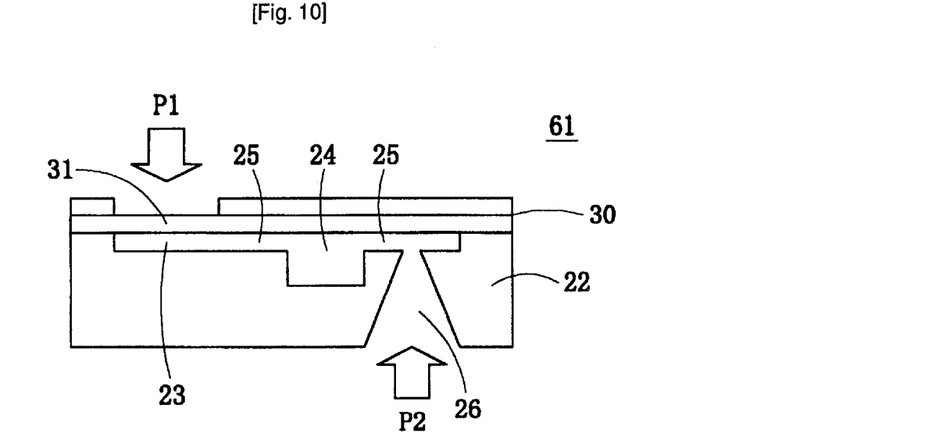
FIG. 10 is a schematic cross-sectional view that shows a structure of a pressure sensor in accordance with still another embodiment of the present invention.

FIG. 10 is a cross-sectional view that shows a construction of a pressure sensor 61 in accordance with still another embodiment of the present invention. In this pressure sensor 61, a pressure-detecting chamber 23 is formed on the upper face of a main-body-side substrate 22 made of a silicon substrate, and a buffer space 24 is formed in the middle of a pressure-directing path 25 connecting a pressure-directing unit 26 and a pressure-detecting chamber 23, formed on the lower face of the main-body side substrate 22. In other words, the pressure-directing paths 25 are placed on both of the sides of the buffer space 24. With this structure, dusts, etc., entered through the pressure-directing unit 26, are captured in the buffer space 24, and less likely to enter the pressure-detecting chamber 23.

Fifth Embodiment

Figure 11A:
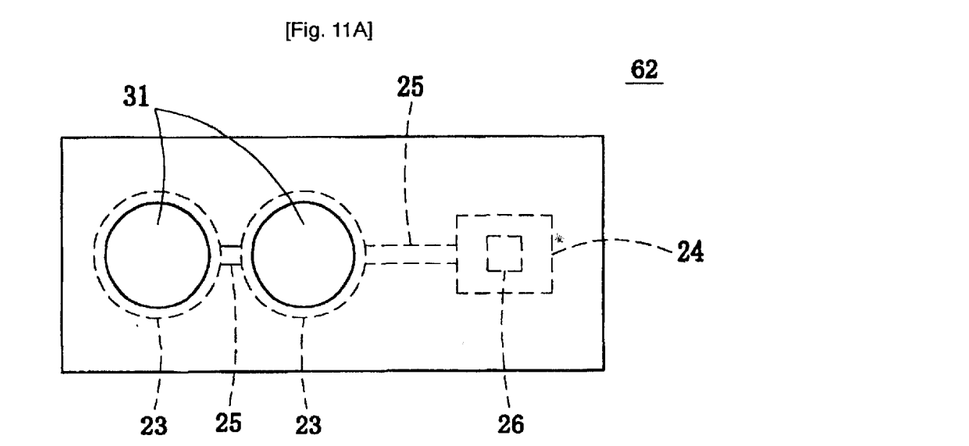
FIG. 11A is a plan view and a cross-sectional view that show a structure of a pressure sensor in accordance with still another embodiment of the present invention.
Figure 11B:
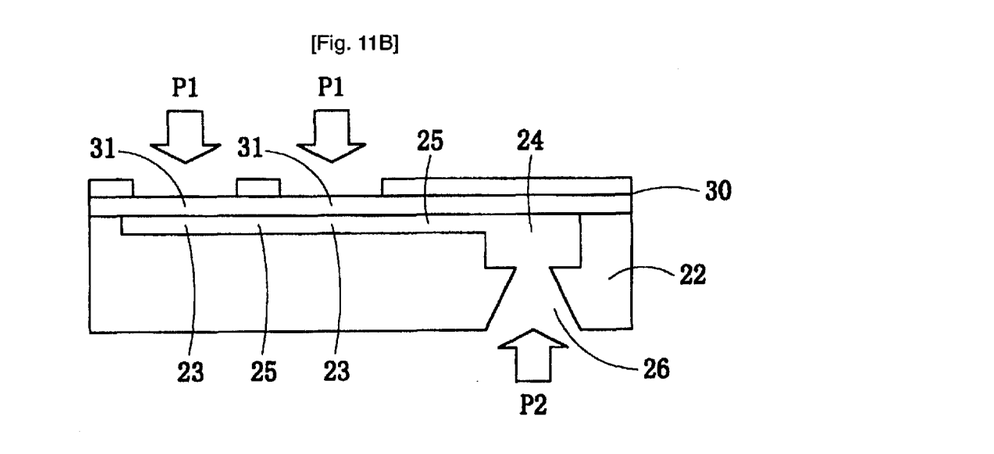
FIG. 11B is a plan view and a cross-sectional view that show a structure of a pressure sensor in accordance with still another embodiment of the present invention.

FIGS. 11A and 11B are a plan view and a cross-sectional view that show a construction of a pressure sensor 62 in accordance with still another embodiment of the present invention. In this pressure sensor 62, a plurality of pressure-detecting chambers 23 and a thin-type diaphragm 31 are installed inside one pressure sensor 62. In the case of an electrostatic pressure sensor manufactured by a method such as sacrifice layer etching, since the depth of the pressure-detecting chamber 23 cannot be increased, it is not possible to make the thin-type diaphragm 31 bigger. In such a case, as explained in the present embodiment, pressure-detecting parts, constituted by a pressure-detecting chamber 23 and a thin-type diaphragm 31, are placed at a plurality of portions and connected to each other, thereby making it possible to increase the electrostatic capacity.

However, in the case when a plurality of pressure-detecting parts are connected in series with each other as shown in this embodiment, the distances from the pressure-introducing unit 26 to the pressure-detecting chamber 23 differ from each other to cause adverse effects on the response characteristics of the pressure sensor.

Even in such a case, as shown in FIGS. 11A and 11B, by placing a buffer space 24 in the pressure-directing path 25 between the pressure-introducing unit 26 and the pressure-detecting chamber 23 closest to the pressure-introducing unit 26, it becomes possible to absorb deviations in the response characteristics to pressure, and consequently to obtain the same sensor characteristics at the respective pressure detecting parts. However, in this case, the shape (cross-sectional area, capacity) of the buffer space 24 is preferably determined so as to make the response frequency further lower than the pressure-detecting part having the lowest response frequency.

Moreover, as shown in this pressure sensor 62, by placing a buffer space 24 in a commonly used portion of the pressure-directing path 25, it becomes possible to miniaturize the pressure sensor 62.

Sixth Embodiment

Figure 12A:
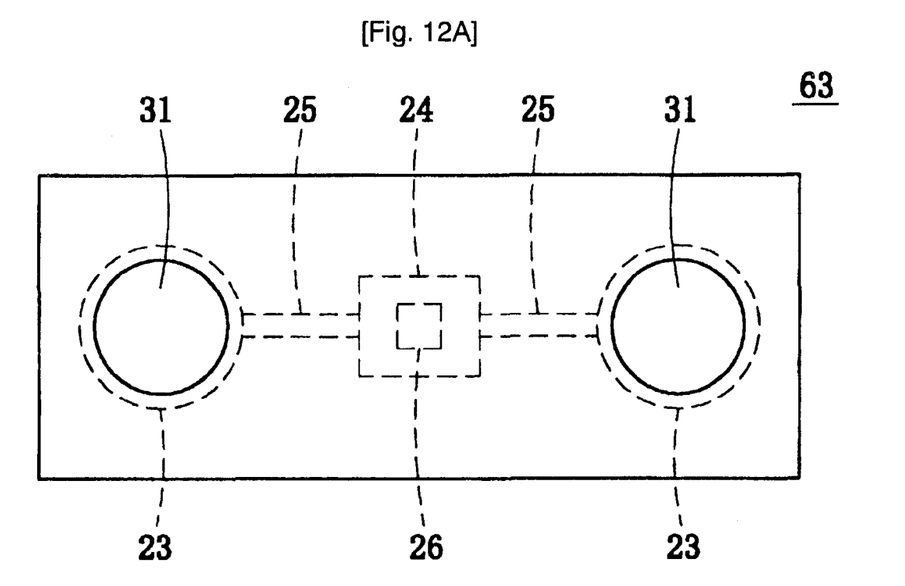
FIG. 12A is a plan view and a cross-sectional view that show a structure of a pressure sensor in accordance with still another embodiment of the present invention.
Figure 12B:
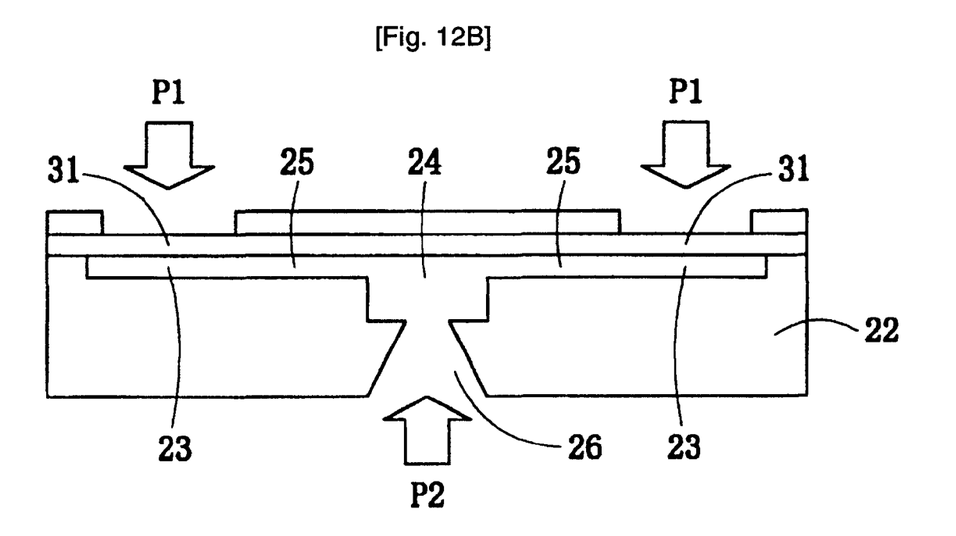
FIG. 12B is a plan view and a cross-sectional view that show a structure of a pressure sensor in accordance with still another embodiment of the present invention.

FIGS. 12A and 12B are a plan view and a cross-sectional view that show a structure of a pressure sensor 63 in accordance with still another embodiment of the present invention. In this pressure sensor 63, a plurality of pressure-detecting parts, each constituted by a pressure-detecting chamber 23 and a thin-type diaphragm 31, are installed inside a single pressure sensor 63 in parallel with each other; therefore, it is possible to make the distances from the pressure-introducing unit 26 to the respective pressure-detecting chambers 23 equal to each other, and consequently to make the response characteristics of the respective pressure-detecting parts uniform with each other. Here, in this pressure sensor 63 also, since the buffer space 24 is placed in a commonly used portion of the pressure-directing path 25, it is possible to miniaturize the pressure sensor 63.

Here, although not shown in the Figures, a buffer space 24 may be placed in each of the pressure-directing paths 25 at an area succeeding the branched pressure-directing paths 25. This arrangement makes it possible to increase the degree of freedom for controlling the response frequency of the pressure sensor.

Seventh Embodiment

Figure 13A:
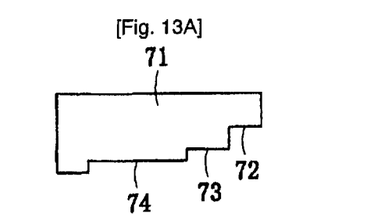
FIGS. 13A to 13F are schematic drawings that explain manufacturing processes of a pressure sensor in accordance with still another embodiment of the present invention.

FIGS. 13A to 13F are schematic drawings that explain manufacturing processes of a pressure sensor in accordance with still another embodiment of the present invention. In this embodiment, as shown in FIG. 13A, trenches are formed on the lower face of a 350 $\mu$m double-sided polish p-type silicon substrate 71 in the order of a dicing trench 72, a polyimide trench 73 and a sensor gap 74. Oxide films are used as masks for forming the respective trenches, and TMAH is used for etching the silicon substrate 71. With respect to the depths of the respective trenches, for example, the dicing trench 72 is set to approximately 10 $\mu$m, the polyimide trench 73 is set to approximately 4 $\mu$m, and the sensor gap 74 is set to approximately 1 $\mu$m. In this case, a buffer space 24 is formed in the silicon substrate 71 simultaneously with the polyimide trench 73, and a pressure-directing path 25 is formed in the silicon substrate 71 simultaneously with the sensor gap 74.

Figure 13B:
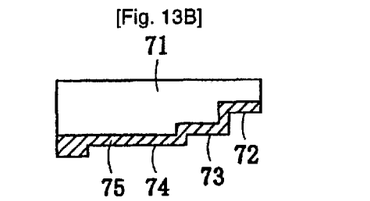

Next, as shown in FIG. 13B, an n-type diffusion layer 75, which forms an etch stop layer at the time when phosphor ions are injected and diffused to carry out m (electrochemical etching), is formed on the lower face of a silicon substrate 71. Moreover, an Al electrode and a contact layer are formed on the lower face of the sensor gap 74.

Figure 13C:
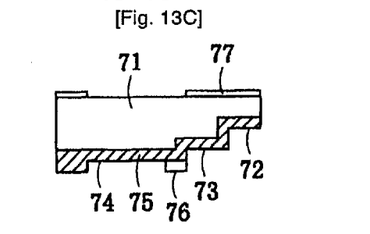
Figure 13D:
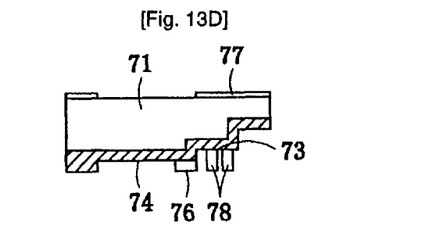

As shown in FIG. 13C, an Al electrode 76 is formed on the above-mentioned contact layer of the sensor gap 74, and the upper face of the silicon substrate 71 is covered with the Si nitride film 77, and the nitride film 77 is patterned so as to serve as a mask at the time when ECE is carried out. Moreover, as shown in FIG. 13D, polyimide 78 is applied to the lower face of the polyimide trench 73, and this is exposed so that the polyimide 78 is patterned.

Figure 13E:
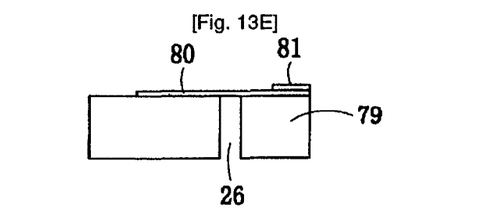

Here, as shown in FIG. 13E, after a metal thin film has been vapor-deposited on the upper face of a glass substrate 79 having a pressure-introducing unit 26 formed in a manner so as to penetrate from the upper face to the lower face thereof, this is patterned to form a fixed electrode 80 and a wire-bonding pad 81.

Figure 13F:
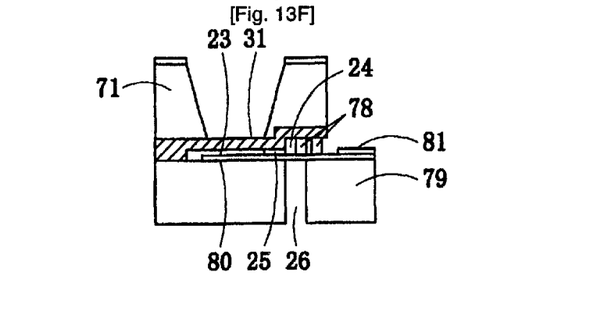

Thereafter, as shown in FIG. 13F, the silicon substrate 71 and the glass substrate 79 are superposed and joined to each other, and the polyimide 78 is made to closely contact the glass substrate 79 so that a space (buffer space 24) between the polyimide trench 73 and the glass substrate 79 and spaces (pressure-detecting chamber 23, pressure-directing path 25) between the sensor gap 74 and the glass substrate 79 are sealed air-tightly. Then, the glass substrate 79 is ECE etched from the opening of the Si nitride film 77 by using KOH (aqueous solution of potassium hydroxide). In this case, the n-type diffusion layer 75 is left as an etch stop layer, and a thin-type diaphragm 31 is formed by the n-type diffusion layer 75.

Next, only the silicon substrate 71 is diced, and one portion of the dicing trench 72 is removed to expose the wire bonding pad 81, and the silicon substrate 71 is finally diced, and divided into respective chips.

Eighth Embodiment

Figure 14:
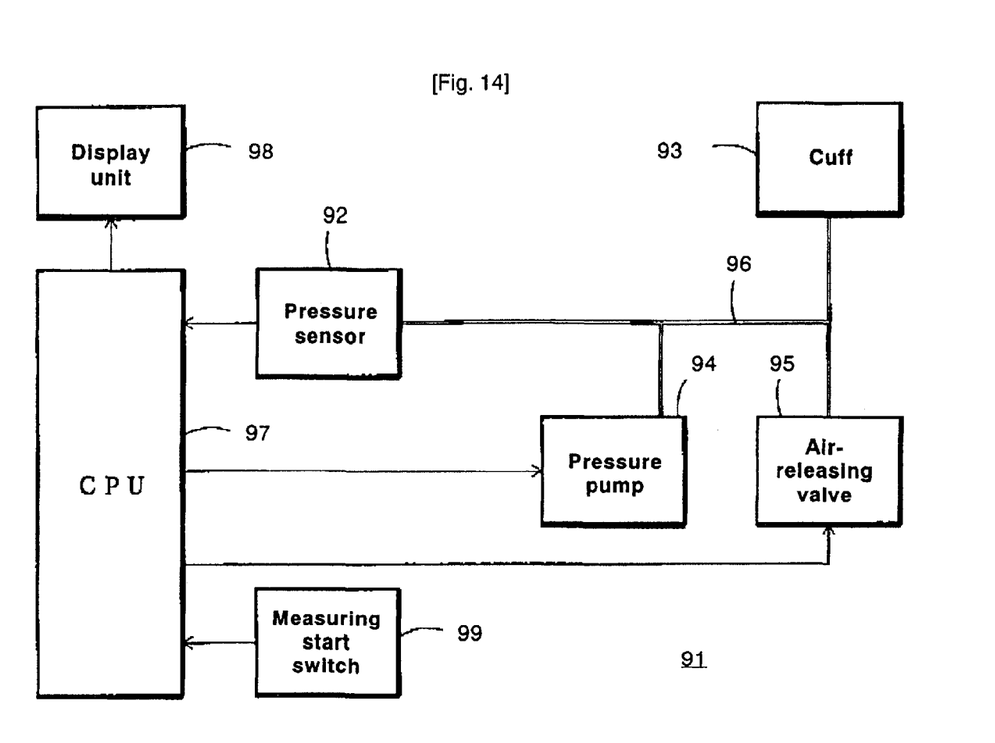
FIG. 14 is a block diagram that shows a structure of a blood pressure meter that is an example of a pressure-measuring apparatus of the present invention.

FIG. 14, which shows another embodiment of the present invention, is a block diagram that shows a construction of a blood pressure meter as an example of the pressure-measuring apparatus of the present invention. This blood pressure meter 91 is provided with a cuff 93, a pressure pump 94 for pressurizing this cuff, an air-releasing valve 95 for reducing the air pressure of the cuff 93, a pressure sensor 92 of the present invention for detecting the cuff, an air path 96 that connects the pressure pump 94, the air-releasing valve 95 and the pressure sensor 92 to each other, a CPU (calculation circuit) 97, a display unit 98 and a measuring-start switch 99.

In accordance with this blood pressure meter 91, pressure noise generated by a pump and a valve can be eliminated so that it is possible to provide a blood pressure meter with a high S/N ratio that can positively hold pulse waves that form a pressure to be detected. Moreover, since it is not necessary to install circuits, etc., which electrically eliminate noise, it is possible to miniaturize the pressure sensor, and also to achieve low prices. In particular, in the case of the application to a pressure sensor used for fingers, it is possible to miniaturize the blood pressure meter, and consequently to provide a convenient meter in use.

EXAMPLES

Figure 15A:
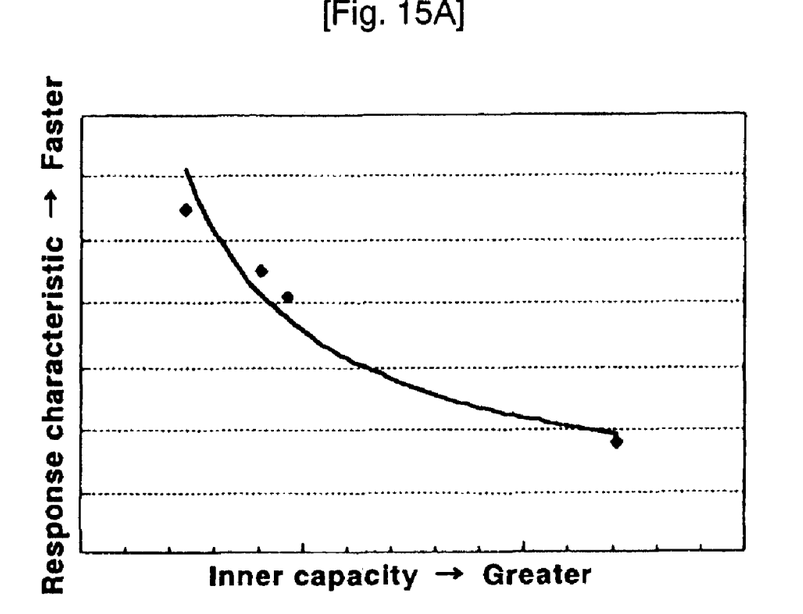
FIG. 15A is a drawing that shows the relationship between the inner capacity of the pressure-detecting chamber and the response characteristic (response frequency), when the cross-sectional area of the pressure-directing path is set to a constant value.

FIG. 15A shows the relationship between the inner capacity of the pressure-detecting chamber and the response characteristic (response frequency), when the cross-sectional area of the pressure-directing path is set to a constant value. Moreover, FIG. 15B shows the relationship between the cross-sectional area of the pressure-directing path and the response characteristic, when the inner capacity of the pressure-detecting chamber is set to a constant value.

Consequently, FIG. 15A indicates that as the inner capacity of the pressure-detecting chamber becomes greater, the response characteristic of the pressure sensor becomes slower exponentially. Therefore, by placing a buffer space in the pressure-directing path so that the capacity of the space including the pressure-detecting chamber and the buffer space is increased; thus, it becomes possible to make the response characteristic of the pressure sensor slower, and also to control the response characteristic by adjusting the cross-sectional area and the capacity of the buffer space.

Figure 15B:
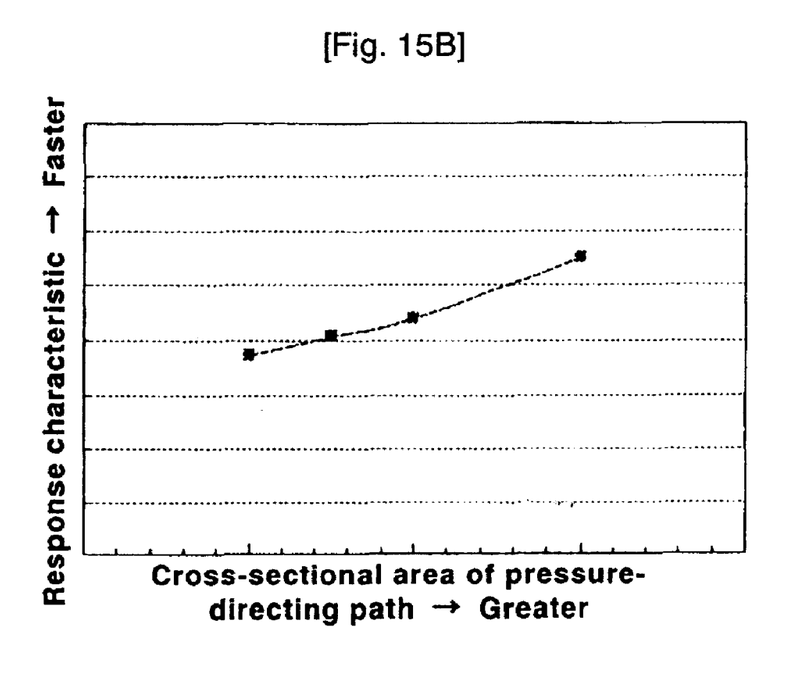
FIG. 15B is a drawing that shows the relationship between the cross-sectional area of the pressure-directing path and the response characteristic, when the inner capacity of the pressure-detecting chamber is set to a constant value.

In contrast, FIG. 15B indicates that on the contrary to expectations, as the cross-sectional area of the pressure-directing path increases, the response characteristic also increases linearly.

In accordance with the pressure sensor of the present invention, since a space having a cross-section that is greater than that of a pressure-directing path is placed in the pressure-directing path connecting a pressure-introducing unit and a pressure-detecting-use cavity; therefore, a pressure (flow of a gas), transmitted through the pressure-directing path, is delayed in the space, and, in the event of a temporary or instantaneous pressure change, the pressure change is absorbed in the space and prevented from reaching the thin-film diaphragm. Therefore, the formation of the above-mentioned space in the pressure-directing path allows the pressure-directing path to have functions of a low-pass filter to pressure. Further, by adjusting the cross-sectional area and the capacity of the space, the degree of delay of the pressure transmission is controlled so that it becomes possible to control the response frequency and cut-off frequency of the pressure sensor with high precision.

Moreover, in accordance with a blood-pressure meter that is one embodiment of the pressure-measuring apparatus of the present invention, since it is possible to eliminate pressure noise that is caused by a pump and a valve, it becomes possible to positively hold pulse waves that form a pressure to be detected, and consequently to achieve a blood pressure meter that has a high S/N ratio. Moreover, since it is not necessary to provide circuits, etc. that electrically eliminate noises, it is possible to miniaturize the pressure sensor, and consequently to achieve low prices. In particular, in the case of the application to a pressure sensor used for fingers, it is possible to miniaturize the blood pressure meter, and consequently to provide a convenient meter in use.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A pressure sensor comprising:
    a semiconductor substrate having a pressure introduction passage therethrough;
    a thin-film diaphragm covering the semiconductor substrate with a predetermined distance therefrom forming a pressure directing path and a pressure detecting chamber therebetween, the thin-film diaphragm covering the pressure detecting chamber being distorted in response to pressure transmitted into the pressure detecting chamber through the pressure introduction passage via the pressure directing path to enable the pressure sensor to detect a pressure based upon a change of the predetermined distance between the semiconductor substrate and the thin-film diaphragm covering the pressure detecting chamber; and
    a buffer concavity formed in the semiconductor substrate at the pressure directing path,
    wherein pressure transmitted into the pressure detecting chamber through the pressure introduction passage is buffered in the buffer concavity so that distortion of the thin-film diaphragm covering the pressure detecting chamber due to an instantaneous pressure is prevented.

2. The pressure sensor according to claim 1, wherein the buffer concavity is formed such that sensor response frequency of the pressure sensor becomes higher than frequencies in a pressure detection range of the pressure sensor and lower than frequencies of pressure noise.

3. The pressure sensor according to claim 2, wherein sensor response frequency of the pressure sensor is not less than one and a half times a maximum frequency in the pressure detection range.

4. The pressure sensor according to claim 1, wherein the thin-film diaphragm is partially reinforced by a reinforcement member attached thereon such that a portion of the diaphragm thin-film that is not reinforced by the reinforcement member forms the pressure detecting chamber.

5. The pressure sensor according to claim 1, wherein the semiconductor substrate is provided with a pressure directing path concavity and a pressure detection portion concavity thereon and both of the cavities are covered by the thin-film diaphragm.

6. The pressure sensor according to claim 5, wherein the buffer concavity is formed deeper than the pressure directing path concavity.

7. The pressure sensor according to claim 1, wherein the pressure introduction passage is formed through the semiconductor substrate in a manner that the passage becomes wider as it goes to a surface of the semiconductor substrate that is not covered by the thin-film diaphragm.

8. The pressure sensor according to claim 1, wherein the buffer concavity is formed adjacent to the pressure introduction passage.

9. The pressure sensor according to claim 1, wherein the buffer concavity is formed on the pressure directing path at a position separated from the pressure introduction passage.

10. The pressure sensor according to claim 1, wherein the semiconductor substrate is provided with a plurality of pressure detecting chamber concavities spaced to each other, and the plurality of pressure detecting chamber concavities are connected each other via the pressure directing path concavity, and the pressure directing path concavities are connected the same buffer concavity in common.

11. A pressure measuring apparatus having a pressure sensor, the pressure sensor comprising:

a semiconductor substrate having a pressure introduction passage therethrough;

a thin-film diaphragm covering the semiconductor substrate with a predetermined distance therefrom forming a pressure directing path and a pressure detecting chamber therebetween, the thin-film diaphragm covering the pressure detecting chamber being distorted in response to pressure transmitted into the pressure detecting chamber through the pressure introduction passage via the pressure directing path to enable the pressure sensor to detect a pressure based upon a change of the predetermined distance between the semiconductor substrate and the thin-film diaphragm covering the pressure detecting chamber; and a buffer concavity formed in the semiconductor substrate at the pressure directing path, wherein pressure transmitted into the pressure detecting chamber through the pressure introduction passage is buffered in the buffer concavity so that distortion of the thin-film diaphragm covering the pressure detecting chamber due to an instantaneous pressure is prevented.

* * * * *